(12) United States Patent
Bechem et al.

(10) Patent No.: US 6,985,225 B2
(45) Date of Patent: Jan. 10, 2006

(54) FLUORESCENCE-MEASURING SYSTEM

(75) Inventors: Martin Bechem, Wuppertal (DE); Wolfgang Paffhausen, Leverkusen (DE)

(73) Assignee: Bayer HealthCare Aktiengesellschaft, Leverkusen (DE)

( * ) Notice: Subject to any disclaimer, the term of this patent is extended or adjusted under 35 U.S.C. 154(b) by 242 days.

(21) Appl. No.: 10/444,681

(22) Filed: May 22, 2003

(65) Prior Publication Data

US 2004/0032589 A1 Feb. 19, 2004

(30) Foreign Application Priority Data

May 24, 2002 (DE) ................................ 102 23 438

(51) Int. Cl.
*G01J 3/30* (2006.01)
(52) U.S. Cl. ..................................... 356/317; 250/458.1
(58) Field of Classification Search ................. 356/317, 356/318, 417, 319, 332; 250/458.1
See application file for complete search history.

(56) References Cited

U.S. PATENT DOCUMENTS

| | | | | |
|---|---|---|---|---|
| 5,355,215 | A | 10/1994 | Schroeder et al. | 356/317 |
| 5,854,684 | A * | 12/1998 | Stabile et al. | 356/440 |
| 5,933,232 | A | 8/1999 | Atzler et al. | 356/317 |
| 6,057,163 | A | 5/2000 | McMillan | 436/172 |
| 6,542,241 | B1 * | 4/2003 | Thorwirth et al. | 356/436 |
| 6,856,390 | B2 * | 2/2005 | Nordman et al. | 356/344 |
| 2003/0010930 | A1 * | 1/2003 | Thorwirth | 250/458.1 |

FOREIGN PATENT DOCUMENTS

| | | |
|---|---|---|
| DE | 19914279 | 7/2000 |
| EP | 0751393 | 2/1997 |
| FR | 2808888 | 11/2001 |
| WO | 9842442 | 1/1998 |

OTHER PUBLICATIONS

Schroeder, K. et al., FLIPR: A New Instrument for Accurate, High Troughput Optical Screening: J. of. Biomolecular Screening, 1, 75-80, (1996).

* cited by examiner

*Primary Examiner*—Layla G. Lauchman

(57) ABSTRACT

The invention relates to a fluorescence-measuring system as can be employed for high-throughput screening in drug development. The arrangement for fluorescence excitation contains a two-dimensionally extended sample-receiving device and at least two illumination sources for exciting the fluorescence of the samples. The illumination sources are extended linearly and arranged in such a way that the illuminated area of the sample-receiving device is homogeneously illuminated directly or via deflecting mirrors at an opening angle of $\leq 30°$. A detector system for the fluorescence light from the sample-receiving device is arranged on either side of the sample-receiving device in such a way that it detects fluorescence emission from the area of measurement at an angle outside the range of reflection of the excitation light of the illumination sources at the illuminated area of the sample-receiving device, preferably at an angle in the range from 80° to 100°, particularly preferably about 90°, to the extended plane of the area of the sample-receiving device.

28 Claims, 8 Drawing Sheets

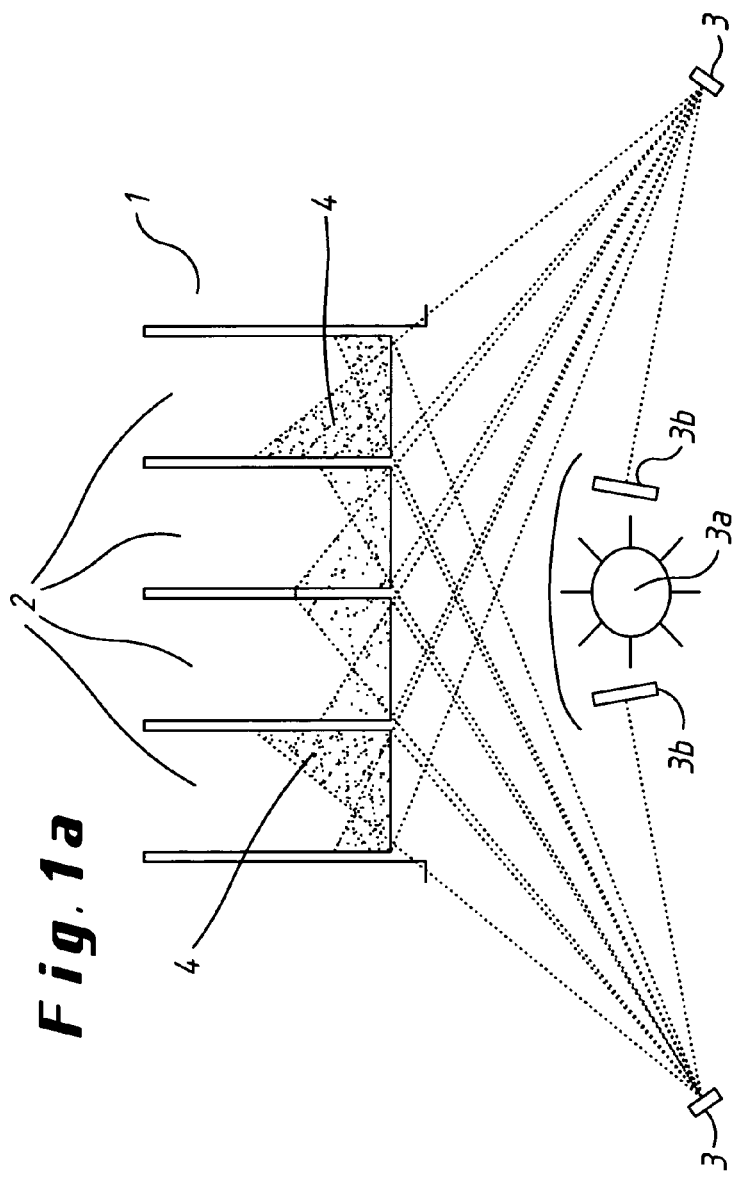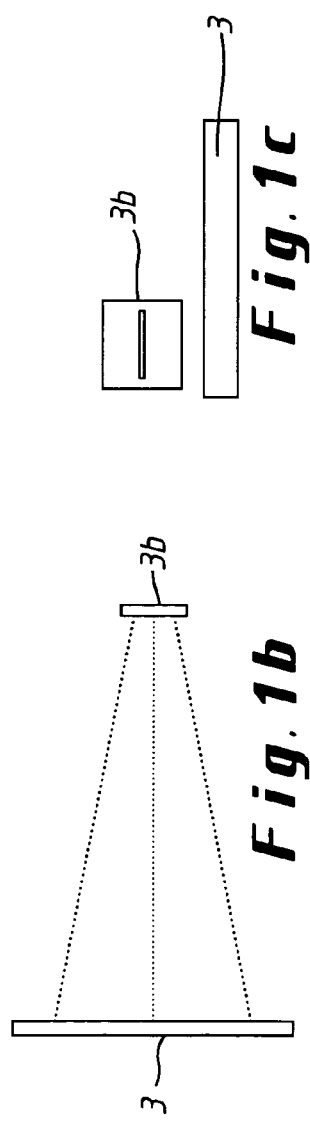

FLUORESCENCE-MEASURING SYSTEM

The invention relates to a fluorescence-measuring system as may be used, for example, for high-throughput screening in drug development.

A common method of detecting or analysing a substance in a contact-free manner is to label the substance with a selected fluorescent dye. Selection of the fluorescent dye generally depends on the physical property to be investigated. For analyses of this type, the labelled substance is illuminated with light of a wavelength or wavelength region which is suited to the absorption behaviour of the fluorescent dye used (usually the absorption maximum). The response of the fluorescent dye comprises emitting the emission light characteristic for the fluorescent dye, whose wavelength is usually longer than that of the exciting radiation. By choosing a suitable labelling fluorescent dye, it is possible to measure quantitatively changes in the physical property, for example concentration of the substance in a solution, via changes in the fluorescence behaviour, for example changes in the fluorescence intensity and/or in the wavelength of the emission peak.

Examples of subclasses of substances are biomolecules (DNA, proteins, lipids) and cell fragments, biological cells or tissues, or organic or inorganic supports ('beads' or 'microspheres') on which biomolecules have been immobilized. The possibility of fluorescently labelling this biological material using suitable techniques is state of the art.

A technique common in drug research is to employ fluorescent methods for evaluating test substances by staining the test system to be investigated (biomolecules and/or cells and/or biomolecules/cells immobilized on supports) with a suitable fluorescent dye so that it is possible hereby to measure changes in parameters via the interaction of test substances. A typical example for this is staining with ion-sensitive fluorescent dyes, as are commercially available, for example, for detecting K+, Ca++ and changes thereof, or else for detecting changes in the membrane potential or intracellular pH.

Frequently, appropriately prepared and fluorescently labelled cells are used in small reaction vessels for such assays. These reaction vessels are typically available on an area of approx. 108 mm×72 mm in a matrix arrangement as "standardized microtitre plates" having a base of approx. 128 mm×86 mm in versions with 96, 384 or 1 536 wells. Biological cells often grow in a nutrient solution on the bottom of the wells and form a "cell layer" which, after appropriate staining, can be excited in many different ways so as to exhibit fluorescence. An automated standard method is the analysis of a microtitre plate with the aid of commercial microtitre plate readers having a fixed geometry for measuring excitation and emission of the fluorescent dye. For an extensive and complete analysis, the microtitre plate is transported electromechanically and sequentially, well-by-well, into the excitation/measurement position. There exist measuring systems with different illuminating geometries for perpendicular excitation and measuring the fluorescence from above or, through the transparent base of microtitre plates, from below, as is described, for example, in DE 197 20 667 A1 (or, in parallel, in U.S. Pat. No. 5,933,232).

Since high-throughput screening for drug research requires several millions of chemical substances to be tested for their action in as short a time as possible, a high rate of measurement is a prerequisite for this high throughput. In the case of conventional fluorescence readers, moving the plate mechanically stands in the way of this. The measurement times for a microtitre plate with 1 536 wells which have to be addressed individually are in the minute range.

The technically more complicated laser-scanning systems (K. Schroeder e.a.: FLIPR: A New Instrument for Accurate, High Throughput Optical Screening; J. of. Biomolecular Screening, Vol 1, Number 2, 1996; U.S. Pat. No. 5,355,215), in which a laser beam excites the cells in all wells of a microtitre plate to emit fluorescence sequentially, albeit approximately simultaneously, due to a very fast guidance of the beam, operate distinctly faster. Scanning with the aid of rotating deflecting mirrors results in a virtually two-dimensional excitation of the objects whose fluorescence is recorded by an integrated image sensor. A diaphragm system minimizes possible background fluorescence. Despite or due to the low dwell time of the laser, however, the local irradiation intensity is very high so that there is the risk of photobleaching of the usually not very light-fast fluorescent dyes and thus of misinterpreting the data. Moreover, the system is limited by the number of excitation wavelengths of the laser. Thus, the common argon ion laser with its excitation maximum at 488 nm is hardly usable for excitation in the near UV, for example at 360 nm. Exchanging the laser is complicated; frequently required (water)-cooling is expensive. Adjustment of the optics is difficult for routine application and can only be carried out by skilled workers; the mechanics (rotating deflecting mirrors) is potentially susceptible to faults.

In very many cases, the supernatant of the cells in the individual wells of a microtitre plate still contains the fluorescent dye used for staining the cells. This is sometimes absolutely necessary (e.g. in the case of disperse dyes for measuring membrane potential); a washing process, however, in which residual dye is washed out by diluting is also problematic. There is no guarantee that, during a washing process, the cell layer is not damaged or that the cells, merely due to flow dynamics during aspiration, do not alter their biological functionality and that the results are not distorted thereby. Moreover, an additional washing step markedly reduces sample throughput.

The illumination geometry of conventional fluorescence-measuring systems, in which the sample is excited perpendicularly from below or from above, proves to be very disadvantageous. If the cell supernatant, as described above, still contains fluorescent dye, then, with the excitation methods mentioned and owing to the excited liquid column in the supernatant, the background signal may be many times greater than the cellular fluorescence change which results from the interaction of a test substance with the cells. The reason for this is the fact that the fluorescently labelled cell monolayer is usually only 10 $\mu$m thick, whereas the supernatant has a height of several millimetres. This leads unavoidably to a distortion of the results.

The quantitative fluorescence analysis thus required a novel homogeneous two-dimensional excitation method which meets the following requirements:

Excitation of a fluorescent dye at least in the UV-VIS region (220 nm–800 nm) at freely selectable wavelength peaks;

Minimization of interfering background signals by a specific illumination geometry;

Increase in the rate of measurement by parallel, i.e. simultaneous, excitation of all samples distributed across the area of measurement and parallel processing using image-producing detection methods (in contrast to sequential measurement);

Avoidance of photobleaching effects by using minimum local radiation power;

Exclusion of mechanically moved components;
Avoidance of complicated optical readjustments after system set-up;
Detection sensitivity comparable to conventional fluorescence-measuring systems.

The object of the invention is achieved by a fluorescence-measuring system having a two-dimensionally extended sample-receiving device and at least two illumination sources for exciting sample fluorescence, which are extended linearly and arranged in such a way that the illuminated area of the sample-receiving device is homogeneously illuminated directly or via deflecting mirrors at an opening angle of $\leq 30°$. The fluorescence-measuring system of the invention furthermore comprises a detector system for the fluorescence light from the sample-receiving device, which is arranged in such a way that it detects fluorescence emission from the area of measurement at an angle outside the range of reflection of the excitation light of the illumination sources at the illuminated area of the sample-receiving device, preferably at an angle in the range from 80° to 100°, particularly preferably about 90°, to the extended plane of the area of the sample-receiving device.

With an essentially horizontal position of the illuminated area of the sample-receiving device, the detector system is arranged above or below the sample-receiving device.

The sample-receiving device may be an assay support such as, for example, a microtitre plate. Typical formats of microtitre plates have 96, 384 or 1 536 wells. The sample-receiving device may be transparent.

The area of the sample-receiving device is illuminated preferably at a homogeneity of ±20%, preferably ±10%. A homogeneity of this kind can be obtained by arranging in each case one of the linear illumination sources at each of two opposite sides of the sample-receiving device. Each of the linear illumination sources illuminates the nearer region of the sample-receiving device with higher intensity than the more distant region, since the intensity I of the excitation light decreases at $I \sim 1/R^2$ with increasing distance R from the illumination source. Due to the inventive geometrical, that is to say symmetrical, arrangement of the illumination sources, the illumination intensity is essentially constant over the entire area. The two linear illumination sources are preferably arranged on each of the two long sides of a rectangular sample-receiving device. However, there may also be, for example, four illumination sources which are arranged in each case in pairs symmetrically on four different sides of the sample-receiving device so that the illumination intensities of the four illumination sources overlap and the illumination intensity is essentially constant over the entire area.

The linear illumination sources may be designed as linear halogen rods, as fluorescent tubes or as LED strips. However, the linear illumination sources are preferably linearly arranged optical fibres which can be arranged from a round fibre bundle in a special arrangement into a fibre cross-section converter. Optical fibres may consist of special polymeric material such as PMMA (polymethylmethacrylate) or PC (polycarbonate) or of standard glass or quartz glass and are suitable in a diameter range from approx. 5 µm to 2 mm. In order to counter inhomogeneities of the irradiation light on the entry side of the light guide, the fibres of the cross-section converter should be randomly mixed.

The linear illumination sources emit a wavelength which corresponds to the excitation wavelength for fluorescence excitation of the samples in the sample-receiving device. The illumination sources can emit coloured light or appropriately filtered white light, for example by introducing the light of appropriate lamps into the fibre cross-section converter on the entry side and making it monochromatic via filters, preferably interference filters. Correspondingly, the illumination sources can also emit light from flashlights for pulsed excitation or from UV lights for fluorescence excitation in the UV region (220–400 nm). Likewise, it is possible to couple into the cross-section converter a continuous laser with appropriate expansion optics adapted to the numerical aperture of the fibre optics. A pulsed laser in the same arrangement provides the possibility of image-producing time-delayed fluorescence measurement (TRF). The usually short fluorescence half-life of the interfering background can, with appropriate fluorescence lifetime of the useful signal, drastically improve the signal-to-noise ratio.

The detector system may contain an imaging detector such as a video measuring system which is preferably equipped with a residual light intensifier. The residual light intensifier may have a gating device which can be used to make the camera sensitive to the useful signal within the nano-second range only after a short laser excitation pulse (in the pico-second range).

One or more filters which select the fluorescence light prior to detection can be arranged between the sample-receiving device and the detector system. A plurality of filters which are intended to be used as an alternative can be arranged in a filter changer.

The fluorescence-measuring system may also have one or more dichroitic mirrors between the sample-receiving device and the detector system, which divide the fluorescence light from the sample-receiving device into two or more wavelengths, which fluorescence light is then selectively coupled out and detected.

The fluorescence-measuring system of the invention has the advantage that an assay support such as, for example, a microtitre plate is completely and simultaneously illuminated and not just the core region of each well.

The fluorescence-measuring system of the invention is format-free. Due to the two-dimensional excitation, it can be applied not only to microtitre plates but to all types of assay supports containing fluorescently labelled assays. Thus it is also possible to evaluate gels on flat substrates.

The fluorescence-measuring system of the invention can be adjusted from the UV to the near infrared region (220–800 nm) by choosing suitable excitation light sources and filters.

Due to simultaneous and parallel measurement of all wells of a microtitre plate, the fluorescence-measuring system of the invention is suitable in particular for kinetic measurements which can be carried out simultaneously on all wells using the fluorescence-measuring system of the invention, thus saving a lot of time in comparison with kinetic measurements using conventional systems.

FIGURES AND EXAMPLES

In the figures,
FIG. 1 shows the principle of homogeneous excitation,
FIGS. 1a, 1b, and 1c illustrate homogeneous illumination via light-deflecting mirrors.
FIG. 2 shows the cross section of a glass fibre cross-section converter,
FIG. 3 shows the structure of a fluorescence-measuring system,
FIG. 3a illustrates a fluorescence-measuring system in which the detector system is located above the sample-receiving device.

Figure 1:
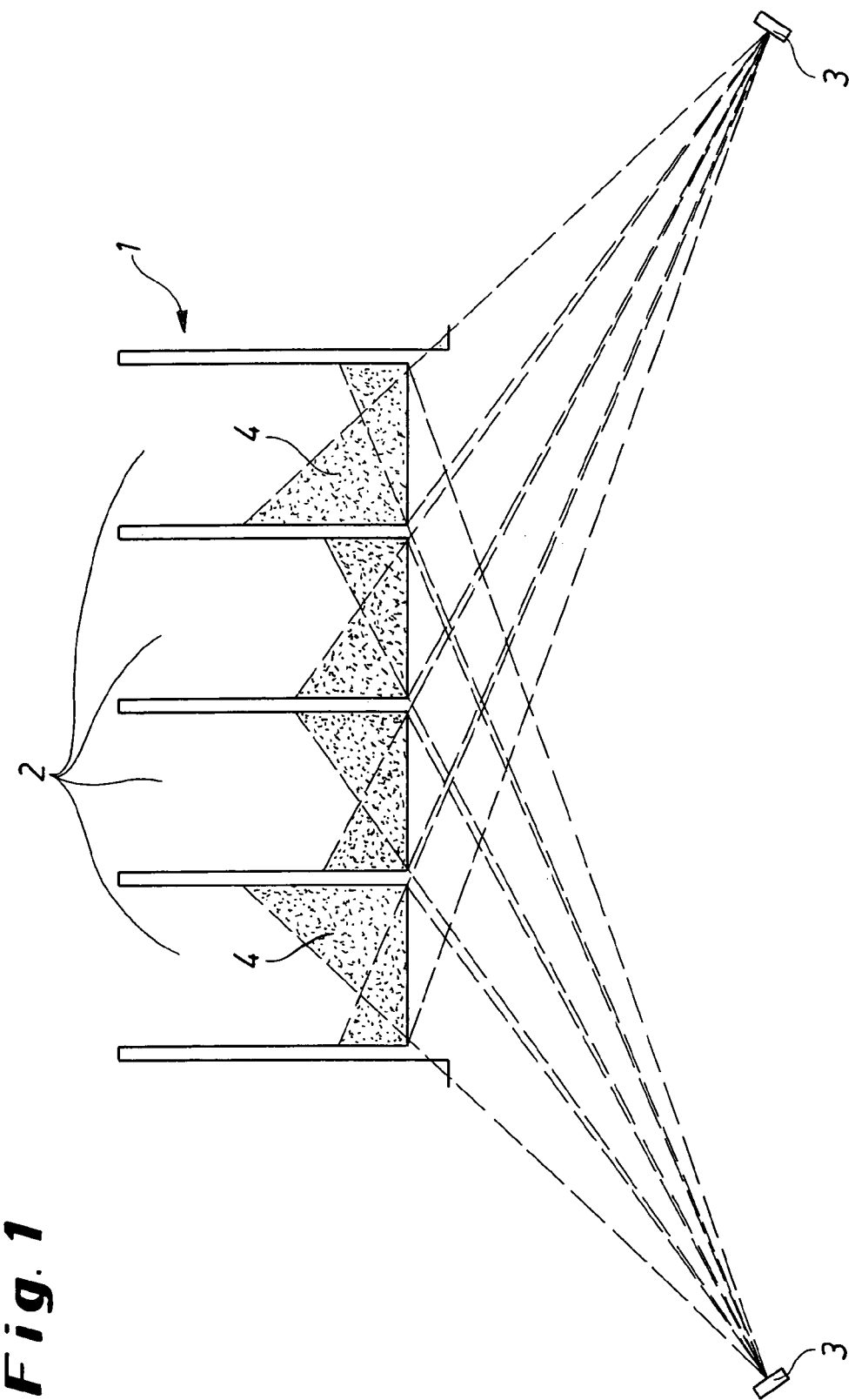

FIG. 1 shows how to obtain a homogeneous illumination of a microtitre plate 1 by using two illumination sources 3. The microtitre plate 1 having the wells 2 is illuminated from below by the two symmetrically arranged illumination sources 3. The volume 4 in the wells 2, illuminated by the illumination sources 3, has a dark colour and is essentially constant for all wells 2.

FIG. 1*a*. shows homogeneous illumination of the microtitre plate 1 wherein the illumination sources 3 are deflecting mirrors which redirect light flowing from light source 3*a* through slit apertures 3*b*. FIG. 1*a* provides a top view and FIG. 1*b* provides a front view of slit apertures 3*b* in relation to the deflecting mirrors 3.

Figure 2:
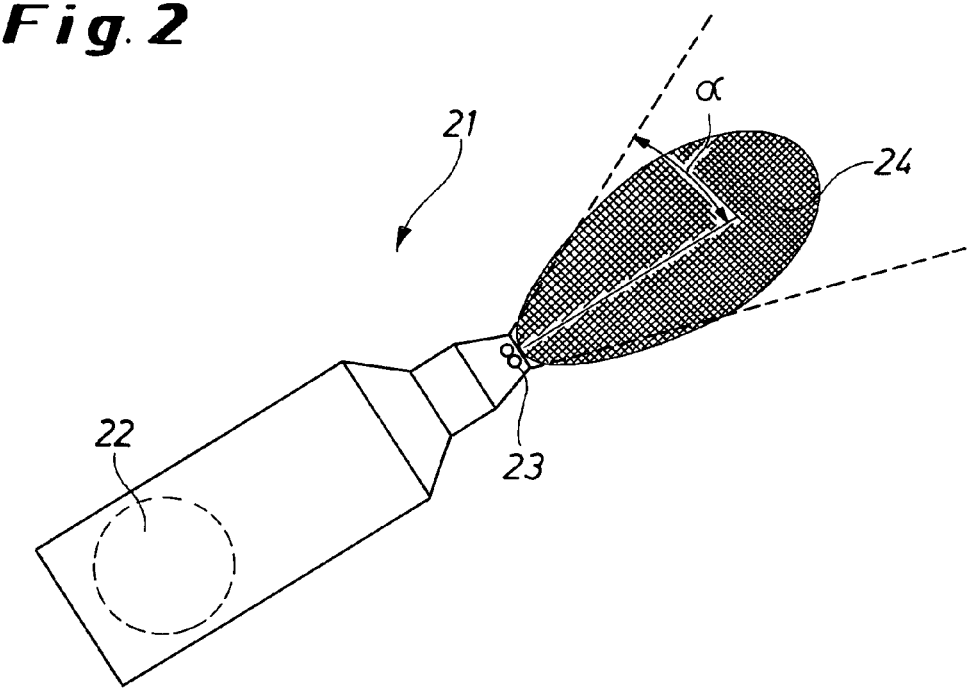

FIG. 2 shows a cross section of a fibre cross-section converter 21. The excitation light is supplied by the optical fibre bundle 22. In the cross-section converter 21, the optical fibres of the bundle 22 are rearranged into a linearly extended strip of fibres 23. The width of the strip is given by the diameter of the initial bundle and is approx. 1 mm for a length of 150 mm and an initial cross section of 15 mm. The emitted light 24 typically, for example with a glass fibre cross-section converter, has an opening angle a of approximately 30°, corresponding to an aperture of 0.5=sin α/2.

Figure 3:
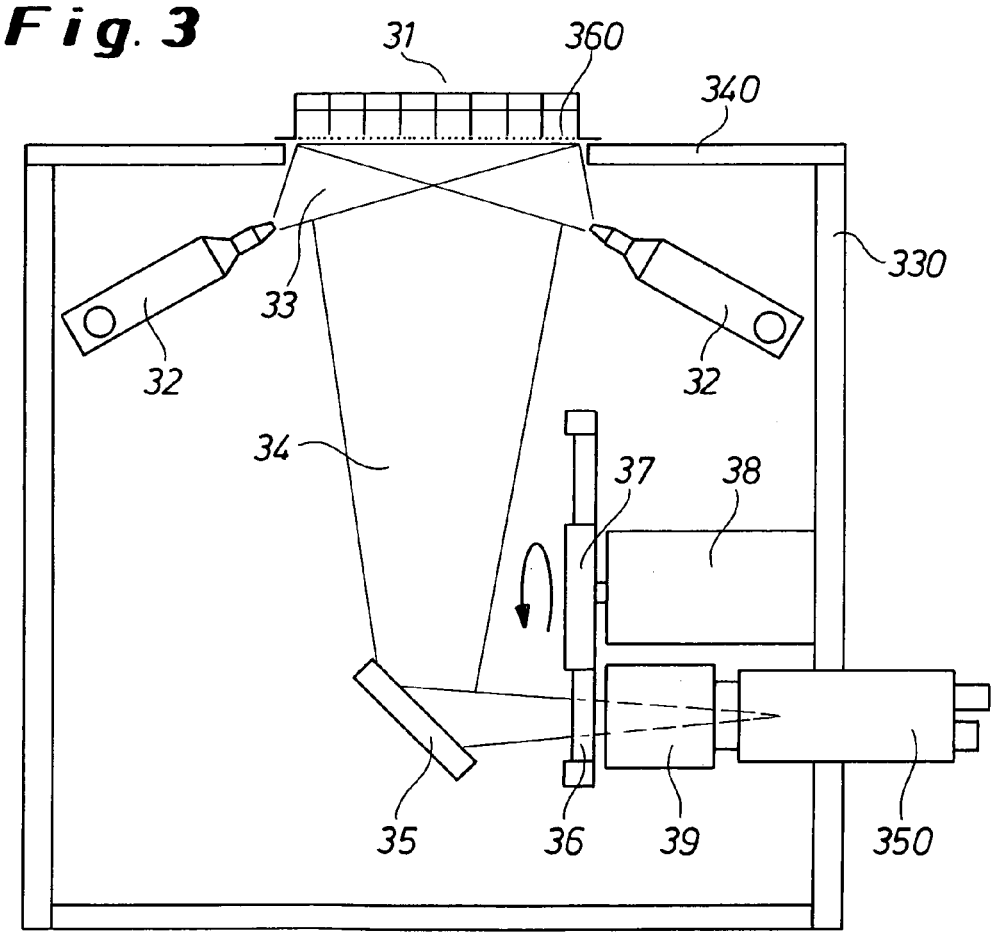

FIG. 3 shows the structure of a fluorescence-measuring system. The fluorescence-measuring system comprises a housing 330 with a lid 340. The lid 340 contains a gap on which a microtitre plate 31 is positioned in such a way that it can be irradiated from the interior of the housing 330. The interior of the housing 330 contains the other components of the fluorescence-measuring system. The microtitre plate 31 having a base of approx. 128 mm×86 mm and a transparent base plate 360 is irradiated by two glass fibre cross-section converters 32 with the excitation light 33 at an angle of approximately 25° through the base plate 360. The two glass fibre cross-section converters 32 are arranged along the 128-mm long sides of the microtitre plate 31. The fluorescence light 34 emitted through the base plate 360 of the microtitre plate 31 is directed via the dichroitic mirror 35 and via a lens 39 to an integrated CCD camera 350. An interference filter 36 which is arranged in a filter wheel 37 is located between the dichroitic mirror 35 and the lens 39. The filter wheel 37 can be rotated with the aid of a motor 38.

Figure 3A:
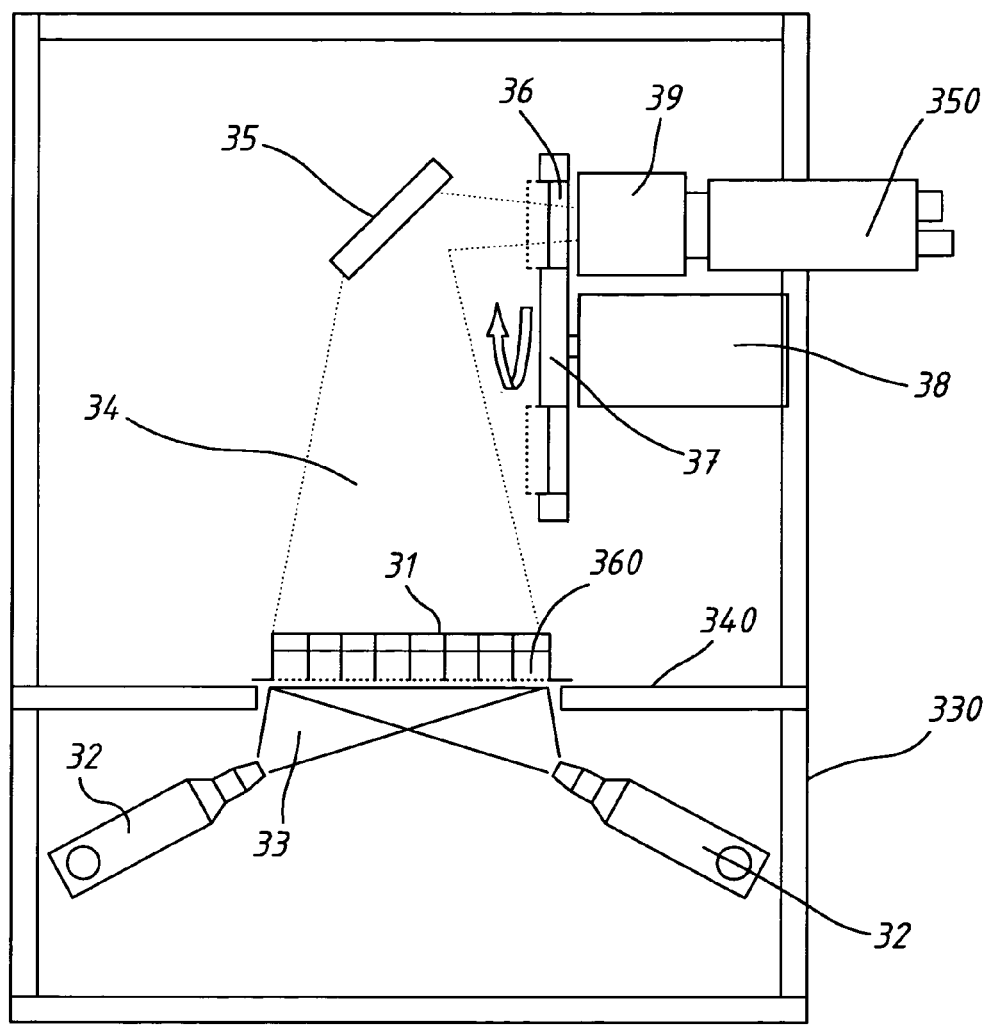

FIG. 3*a* shows the fluorescence-measuring system located above the microtitre plate 31.

Figure 4:
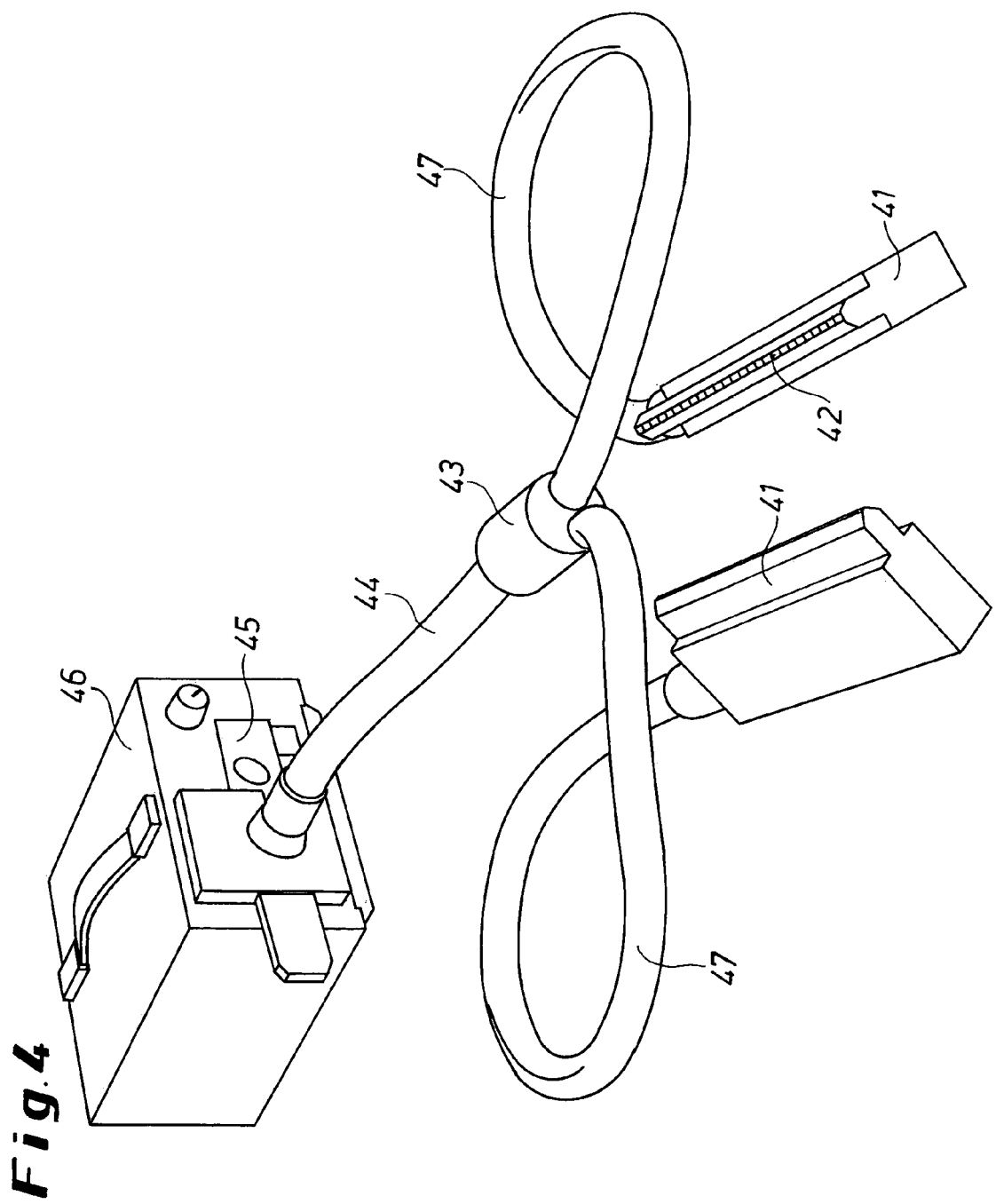
FIG. 4 shows the illumination system with two cross-section converters.

FIG. 4 shows an illumination system with two fibre cross-section converters 41. The incident light for the fibres is generated by a lamp unit 46. It is possible, via a filter slider 45, to filter light of different wavelengths out of the excitation spectrum of the lamp unit 46. The optical fibres are randomly mixed in the fibre-mixing section 44 and divided into two strands 47 at the distributor piece 43. The fibre cross-section converters 41 with the linearly arranged fibre exit areas 42 are located at the ends of the strands 47.

Figure 5:
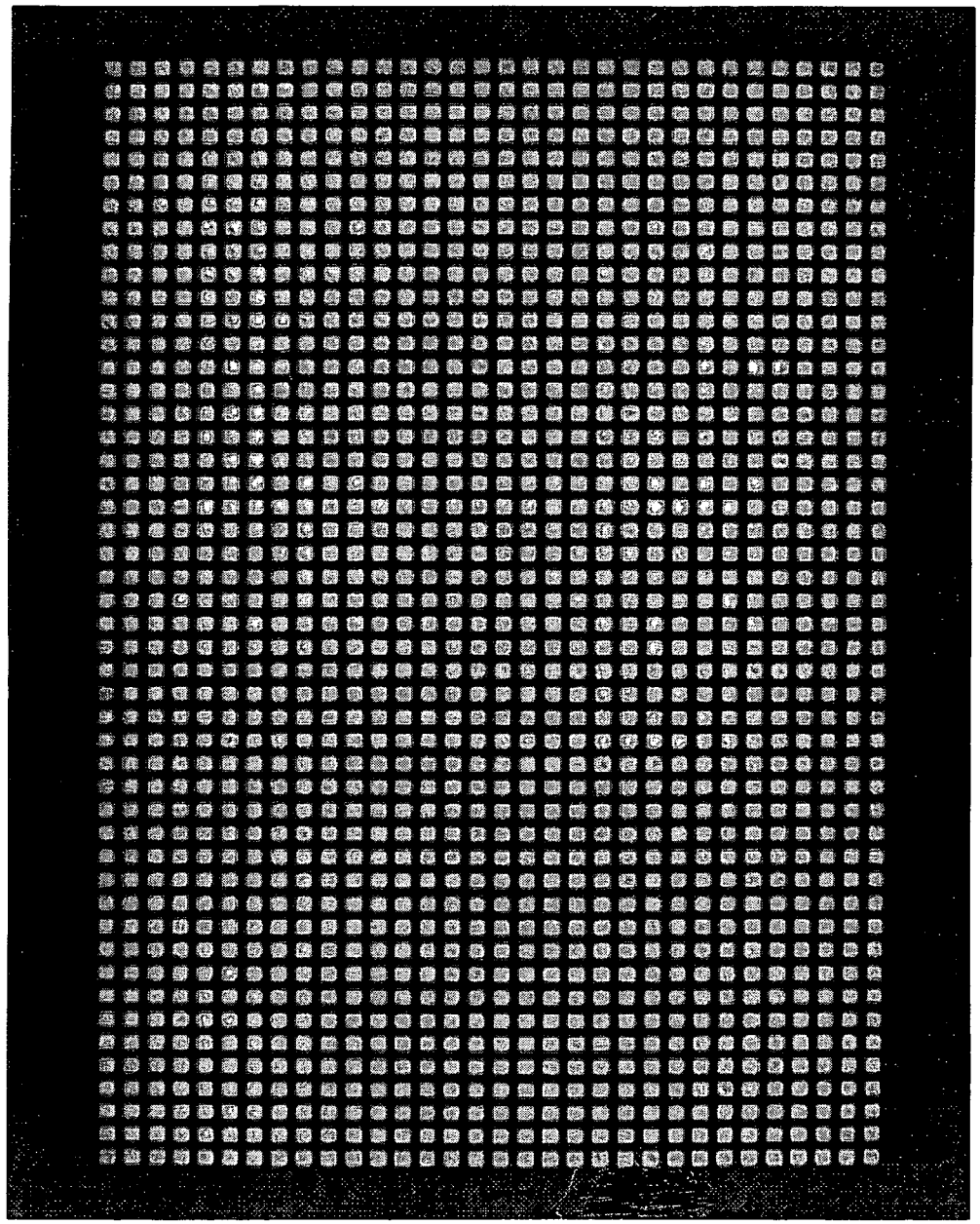
FIG. 5 shows the results of measuring on a 1 536-well microtitre plate.

FIG. 5 shows an example for measuring fluorescence emission from the wells of a 1 536-well microtitre plate using the fluorescence-measuring system of the invention. All wells contain the same fluorescence solution. The homogeneous illumination results in a microtitre-plate image in which the emission of all wells exhibits the same brightness within the preset tolerance limits.

Figure 6:
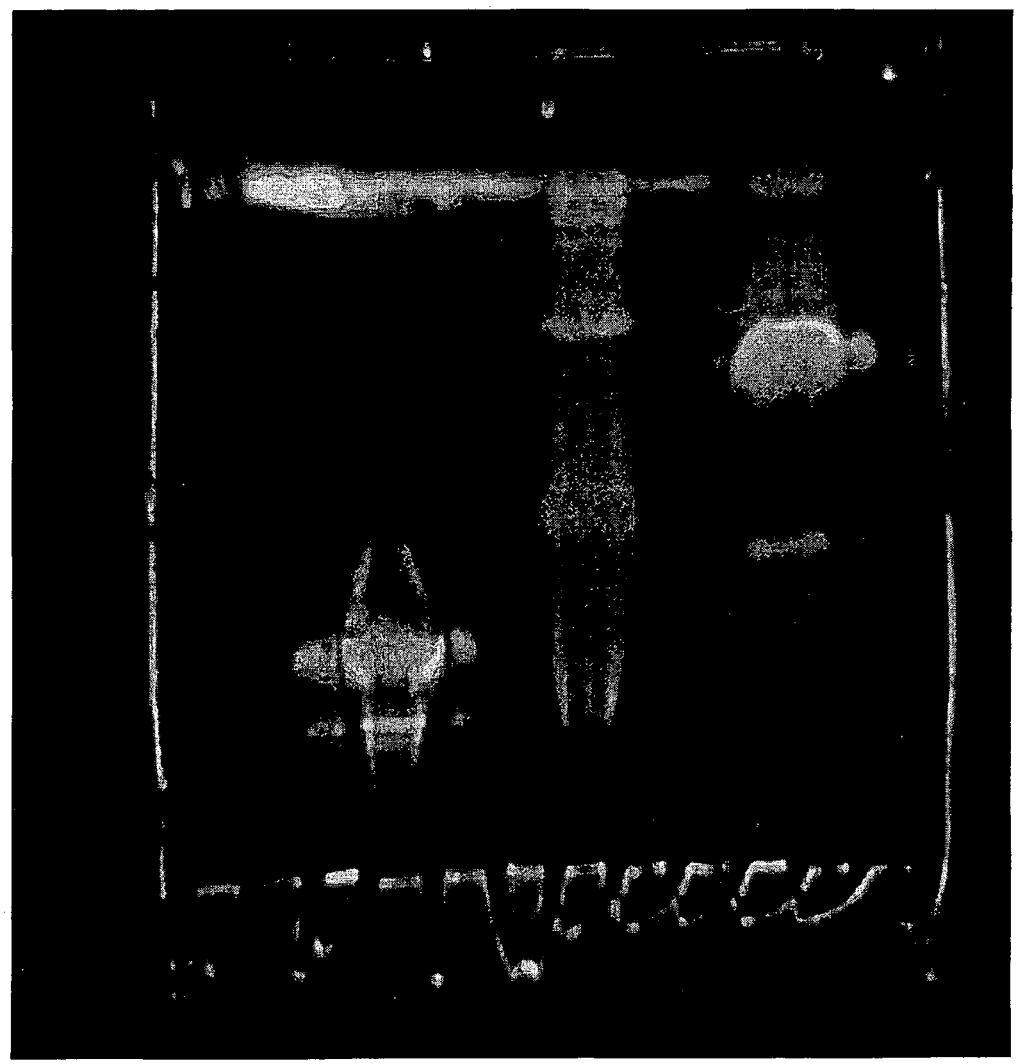
FIG. 6 shows format-free measurement of fluorescence emission on a fluorescent dye-labelled DNA electrophoresis gel.

FIG. 6 shows an example of measuring the fluorescence emission from two-dimensional objects using the fluorescence-measuring system of the invention. This example is the image of a DNA electrophoresis gel labelled with a fluorescent dye. In contrast to conventional gel-imaging technology in which, for example, the DNA gel is stained with the harmful fluorescent dye ethidium bromide (potentially mutagenic/carcinogenic) and is excited in the short-wavelength UV region (360 nm) (protective goggles), it is possible, with the aid of the homogeneous two-dimensional simultaneous excitation and due to the free choice of excitation and emission wavelengths, to switch to the harmless DNA fluorescence-gel dye SYBR-Green (excitation: 490 nm, emission: 520 nm).

Figure 7:
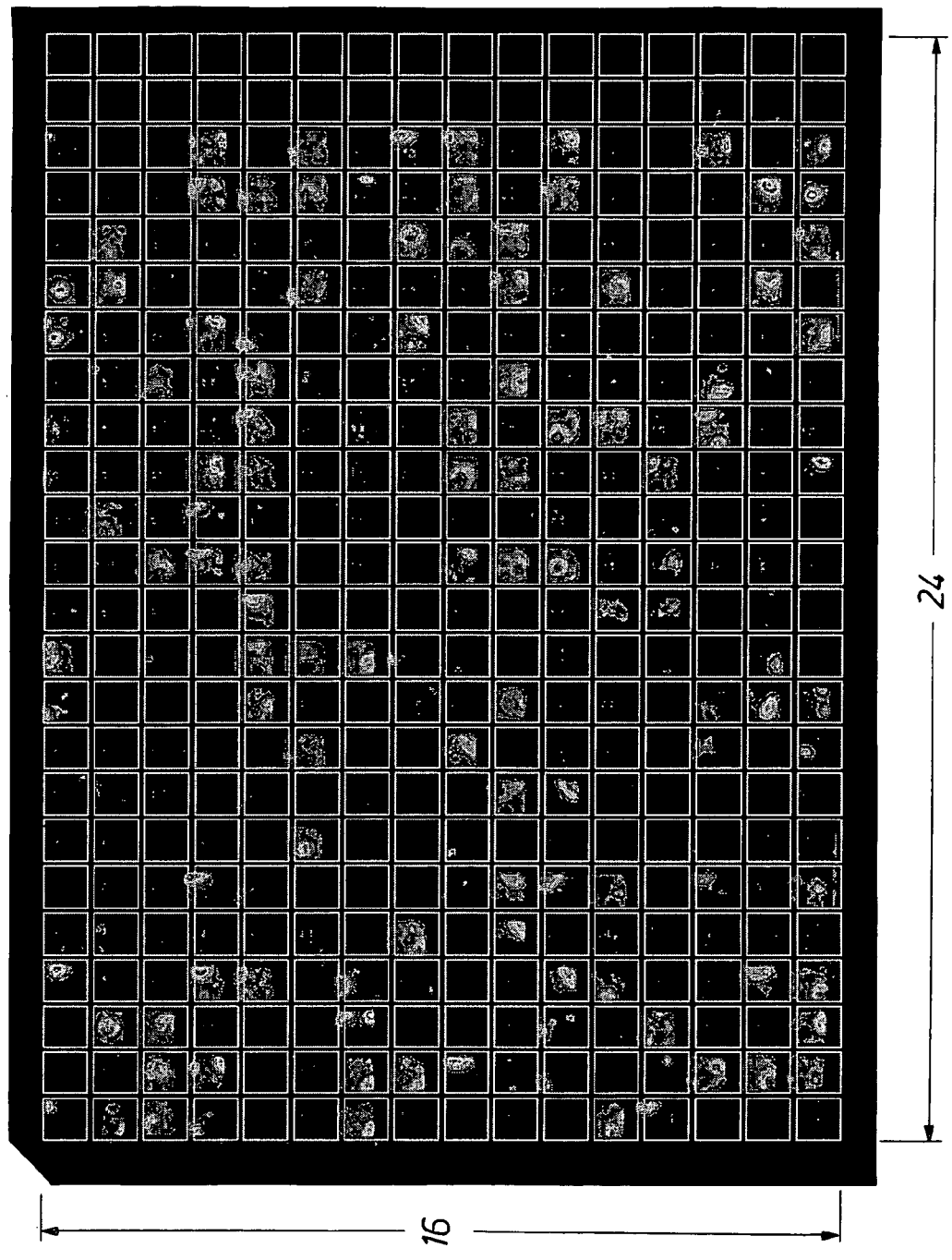
FIG. 7 shows space-resolved measurement of fluorescence emission from the wells of a 384-well microtitre plate using the fluorescence-measuring system of the invention.

FIG. 7 shows an example of measuring the fluorescence emission from the wells of a 384-well microtitre plate (24×16 wells) in a space-resolved manner using the fluorescence-measuring system of the invention. Each well contains various cell clones which express a fluorescent protein, the "GFP (green fluorescent protein)" to different degrees. The search is for the clone having the highest expression. It is obvious that the average from a single well (principle: fluorescence reader) produces false data/information, since those cells whose fluorescence is particularly bright, that is to say which exhibit good expression, can be identified in a single well only via the spatial resolution.

What is claimed is:

1. A fluorescence-measuring system, having
a two-dimensionally extended sample-receiving device (1, 31) and illumination sources (3, 21, 32, 41) for exciting sample fluorescence, characterized in that,
the illumination sources (3, 21, 32, 41) are extended linearly and at least two illumination sources (3, 21, 32, 41) are arranged in such a way that the illuminated area of the sample-receiving device is homogeneously illuminated directly or via deflecting mirrors at an opening angle of $\leq 30°$, and in that
a detector system (350) for the fluorescence light from the sample-receiving device is arranged on either side of the sample-receiving device in such a way that it detects fluorescence emission from the area of measurement at an angle outside the range of reflection of the excitation light of the illumination sources at the illuminated area of the sample-receiving device.

2. The fluorescence-measuring system of claim 1, wherein the sample-receiving device (1, 31) is transparent.

3. The fluorescence-measuring system of claim 1, wherein the sample-receiving device (1, 31) has a transparent base (360) and illumination by the illumination sources (3, 21, 32, 41) occurs through said transparent base (360).

4. The fluorescence-measuring system according to any of claims 1 to 3, wherein the sample-receiving device (1, 31) is an assay support.

5. The fluorescence-measuring system of claim 4, wherein the assay support is a microtitre plate.

6. The fluorescence-measuring system of claim 1, wherein the area of the sample-receiving device (1, 31) is illuminated at a homogeneity of ±20%.

7. The fuorescence-measuring system of claim 1, wherein in each case a linear illumination source (3, 21, 32, 41) is arranged on each of two opposite sides of the sample-receiving device (1, 31).

8. The fluorescence-measuring system of claim 1, wherein in each case a linear illumination source is arranged on each of the two long sides of a rectangular sample-receiving device (1, 31).

9. The fluorescence-measuring system of claim 1, wherein four illumination sources (3, 21, 32, 41) are present which are arranged in each case in pairs symmetrically on four different sides of the sample-receiving device (1, 31).

10. The fluorescence-measuring system of claim 1, wherein the linear illumination sources (3, 21, 32, 41) are designed as linear halogen rods, as fluorescent tubes or as LED strip.

11. The fluorescence-measuring system according of claim 1, wherein the linear illumination sources (3, 21, 32, 41) are designed as linearly arranged optical fibre guides.

12. The fluorescence-measuring system of claim 11, wherein the optical fibres (22) of the linearly arranged light guides are mixed in a random manner.

13. The fluorescence-measuring system of claim 1, wherein the linear illumination sources (3, 21, 32, 41) emit light of a wavelength which corresponds to the excitation wavelength of fluorescence excitation of the samples in the sample-receiving device (1, 31).

14. The fluorescence-measuring system of claim 1, wherein the illumination sources (3, 21, 32, 41) emit coloured light or appropriately red hot white light.

15. The fuorescence-measuring system of claim 1, wherein the illumination sources (3, 21, 32, 41) emit light from flashlights for pulsed excitation or from UV lights for fluorescence excitation in the UV region.

16. The fluorescence-measuring system of claim 1, wherein the illumination sources (3, 21, 32, 41) emit light from a continuous or pulsed laser which has been adapted to the entry-side numerical aperture of an optical fibre bundle by using appropriate input coupling optics.

17. The fluorescence-measuring system of claim 1, wherein the detector system (350) contains an imaging detector.

18. The fluorescence-measuring system of claim 17, wherein the imaging detector is a video measuring system.

19. The fluorescence-measuring system of claim 1, wherein it has one or more filters (36) between the sample-receiving device (1, 31) and the detector system (350), which can select the fluorescence light prior to detection.

20. The fluorescence-measuring system of claim 19, wherein a plurality of filters (36) are arranged in a filter changer (37).

21. The fluorescence-measuring system of claim 1, wherein it has one or more diebroitic mirrors (35) between the sample-receiving device (1, 31) and the detector system (350), which make it possible to divide the fluorescence light from the sample-receiving device (1, 31) into two or more wavelengths, followed by selective output coupling of said fluorescence light.

22. The fluorescence-measuring system of claim 1, wherein the illuminated area of the sample-receiving device is in an essentially horizontal position and the detector system is arranged above or below the sample-receiving device.

23. The fluorescence-measuring system of claim 1 wherein the detector system (350) is located at an angle in the range from 80° to 100° to the extended plane of the area of the sample-receiving device (1, 31).

24. The fluorescence-measuring system of claim 23 wherein the detection system is located at an angle of about 90° to the extended plane of the area of the sample-receiving device (1, 31).

25. The fluorescence-measuring system of claim 5, wherein the microtitre plate has a format of 96,384 or 1,536 test wells.

26. The fluorescence-measuring system of claim 1, wherein the area of the sample-receiving device (1, 31) is illuminated at a homogeniety of ±10°.

27. The fluorescence-measuring system of claim 18 wherein the video measuring system is equipped with a residual light intensifier.

28. The fluorescence-measuring system of claim 27, wherein the residual light intensifier has a gating device.

* * * * *